US007736889B2

(12) United States Patent
Rife et al.

(10) Patent No.: US 7,736,889 B2
(45) Date of Patent: Jun. 15, 2010

(54) FLUIDIC FORCE DISCRIMINATION

(75) Inventors: Jack C. Rife, Washington, DC (US);
Lloyd J. Whitman, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 163 days.

(21) Appl. No.: 10/457,705

(22) Filed: Jun. 10, 2003

(65) Prior Publication Data

US 2004/0253744 A1   Dec. 16, 2004

(51) Int. Cl.
C12M 1/36 (2006.01)
C12M 1/38 (2006.01)
C12M 3/00 (2006.01)

(52) U.S. Cl. .............. 435/286.5; 436/517; 436/535; 435/283.1; 435/287.1; 435/962; 422/81

(58) Field of Classification Search .......... 356/73, 356/336, 338; 204/554; 422/22, 63, 65, 422/10; 435/7.1–7.92, 41, 243, 5, 283.4–288; 436/518, 526
See application file for complete search history.

(56) References Cited

U.S. PATENT DOCUMENTS

| | | | | |
|---|---|---|---|---|
| 3,893,898 A | * | 7/1975 | Candor | ................ 204/554 |
| 4,670,381 A | * | 6/1987 | Frickey et al. | ............ 435/7.93 |
| 5,922,615 A | * | 7/1999 | Nowakowski et al. | ....... 436/518 |
| 5,981,297 A | | 11/1999 | Baselt | |
| 6,063,589 A | * | 5/2000 | Kellogg et al. | ................ 435/24 |
| 6,086,821 A | | 7/2000 | Lee | |
| 6,097,485 A | * | 8/2000 | Lievan | ................ 356/338 |
| 6,180,418 B1 | | 1/2001 | Lee | |
| 6,267,858 B1 | * | 7/2001 | Parce et al. | ................ 204/600 |
| 6,297,060 B1 | * | 10/2001 | Nowakowski et al. | ....... 436/518 |
| 6,368,553 B1 | | 4/2002 | Lee | |
| 6,568,052 B1 | * | 5/2003 | Rife et al. | ................ 29/25.35 |
| 6,592,820 B1 | * | 7/2003 | Hardman et al. | ............ 422/65 |
| 2002/0119470 A1 | | 8/2002 | Nerenberg et al. | |

OTHER PUBLICATIONS

Tamanaha et al, Hybrid macro-micro fluidics system for a chip-based biosensor, Feb. 2002, J Micromech Microeng, 12, N7-N17.*

(Continued)

*Primary Examiner*—N. Yang
(74) *Attorney, Agent, or Firm*—John J Karasek; Amy Ressing

(57) ABSTRACT

This invention describes a method of using controlled fluidic forces to improve the performance of a biochemical binding assay where a target molecule is captured by specific molecular recognition onto a substrate surface with an affinity coating, and then labeled with a detectable micrometer-scale particle using a second specific molecular recognition reaction with the target. By using specific ranges of label sizes and laminar flow conditions, controlled fluidic forces can be applied to the label particles in order to selectively remove molecules bound to a surface according to their binding strength, and thereby increase the ratio of specifically bound labels to more weakly attached non-specifically bound labels. This method can be used with a wide variety of label types and associated detection methods, improving the sensitivity and selectivity of a broad range of binding assays.

2 Claims, 4 Drawing Sheets

OTHER PUBLICATIONS

Edelstein et al, The BARC biosensor applied to the detection of biological warfare agents, 2000, Biosensors & Bioelectronics, 14, 805-813.*

Tamanaha et al, Magnetic Method for DNA detection on an arrayed solid state device, 2001, Micro Total Analyisis Systems 2001, 444-446.*

Pierres et al, Dissecting streptavidin-biotin interaction with a laminar flow chamber, 2002, Biophys J, 82, 3214-3223.*

Zocchi, Force Measurements on Single Molecular Contacts though Evanescent Wave Microscopy, Biophys J. Nov. 2001, p. 2946-2953, vol. 81, No. 5.

Chang et al, Influence of Direction and Type of Applied Force on the Detachment of Macromolecularly-Bound Particles from Surfaces, Langmuir, 12 (9), 2271-2282, 1996.

Graham, et al, Magnetoresistive-based biosensors and biochips; TRENDS in Biotechnoloby, vol. 22, No. 9, pp. 455-462, Sep. 2004.

Wang, et al, Towards a magnetic microarray for sensitive diagnostics, Jnl. Of Magnetism and Magnetic Mat 293 (2005) pp. 731-736.

Miller, et al., A DNA array sensor utilizing magnetic microbeads and magnetoelectronic detection, Journal of Magnetism and Magnetic Materials, 225 (2001) 138-144.

* cited by examiner

FLUIDIC FORCE DISCRIMINATION

BACKGROUND OF THE INVENTION

1. Field of the Invention

This invention pertains to a method to selectively remove molecules bound to a surface according to their binding strength by attaching micrometer-scale particles to the bound molecules and then applying controlled, laminar fluidic forces to the particles. Such "fluidic force discrimination" (FFD) can be used to improve the sensitivity and selectivity of biochemical binding assays in many fields of use, including forensics, agriculture, medical diagnostics, food and water safety, and anti-terrorism.

2. Description of Related Art

Binding assays such as immunoassays, DNA hybridization assays, and receptor-based assays are widely used to detect trace quantities of specific target molecules contained in a complex sample. Typically, a solid substrate is coated with receptor molecules that have a specific binding affinity for the target. When a liquid sample containing the target is applied to the substrate, the target biomolecules are captured onto the surface by molecular recognition. This capture can be accomplished via any specific ligand-receptor combination such as antibody-antigen or other specific binding combination such as complementary sequences of polynucleic acids (DNA, RNA, or PNA).

Figure 1:
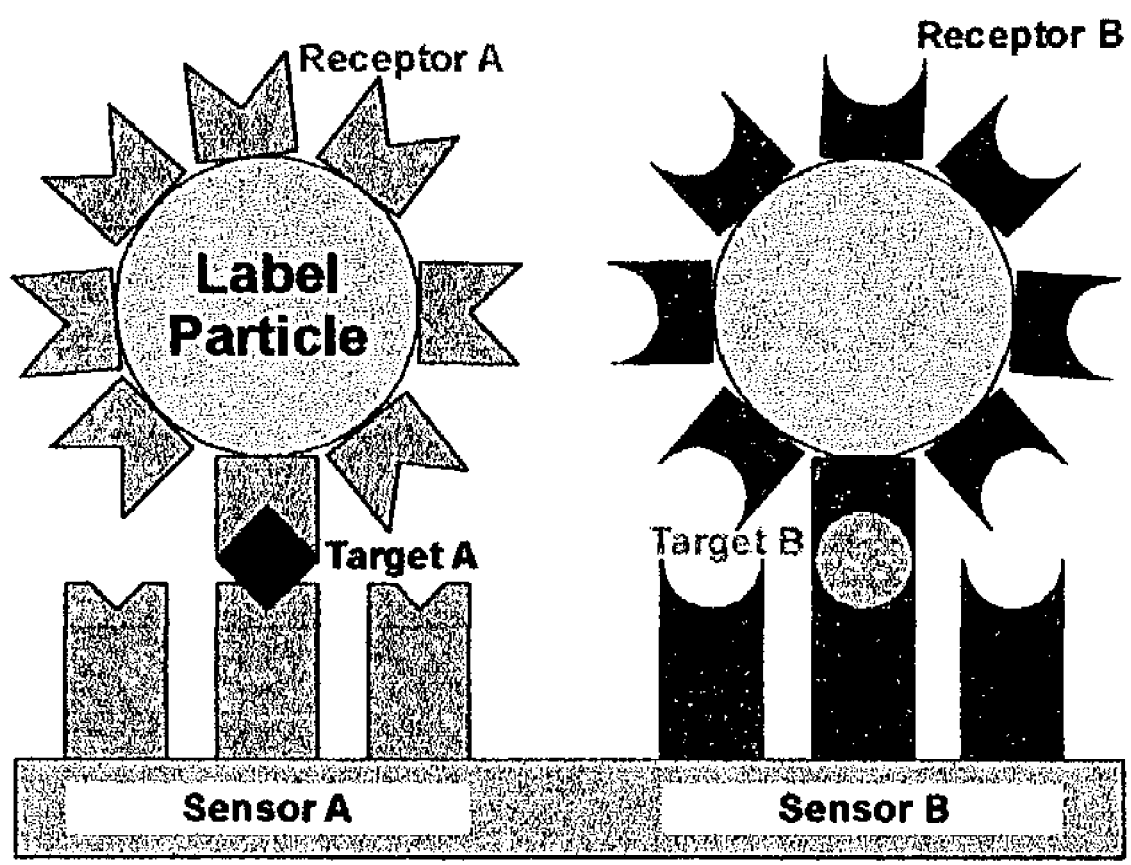

A common approach to detecting captured target molecules is to chemically attach to them a label that generates an observable signal. For example, a label can include a radioactive isotope, enzyme, fluorescent molecule(s) or magnetic particle. The attachment can be made via any chemical means, but is usually made with very strong attachment chemistry such as covalent or aminated electrostatic bonding, or via high-affinity molecular recognition to a second, exposed part of the captured target molecule. The label is detected by appropriate means as a measure of the concentration of the target in the sample. Detection methods have been developed based on a range of transduction mechanisms, including optical, electrical, magnetic, radioactive, electrochemical, thermal, and piezoelectrical. One example is illustrated in FIG. 1 for a case where a plurality of capture molecules specific to different targets are separately immobilized on a substrate with built-in sensors for the label particles. Note that for micrometer-scale labels this illustration is not to scale: the target and receptor molecules are typically 10 to 1000 times smaller than the labels.

There are many variants to binding assays using labels, but a common goal is to measure the concentration of the target with as much sensitivity and selectivity as possible. As long as a sufficient number of labels are present to generate a detectable signal, the sensitivity and selectivity of a binding assay can be limited by labels bound to the surface but not bound to a captured target (sometime referred to as "background" signal). Such labels may be attached to molecules that were also present in the sample and have bound to the surface through relatively weak, non-specific bonds. Alternately, labels may be directly bound to the surface by buoyant weight and/or non-specific bonds. The ability to selectively remove labels bound non-specifically to the surface can greatly improve the sensitivity and selectivity of a binding assay by lowering the minimum number of labels that can be associated with confidence with the intended target, and reducing the likelihood of wrongly associating detected labels with captured target, respectively.

It is possible to selectively remove labels bound non-specifically to a surface in a binding assay by applying a force to the labels sufficient to break weak, non-specific bonds but too small to remove those labels bound by the stronger bonds of specific molecular recognition. On surfaces specially prepared to inhibit non-specific binding, forces on the order of 1 pN are required for this purpose. It is also possible to use the application of forces to label particles for the purpose of selectively breaking specific bonds of increasing strength and thereby either measure the rupture force or identify the bound target based on the rupture force. Forces>10 pN and as large as 1 nN may be required for this purpose. U.S. Pat. Nos. 5,981,297 and 6,180,418 describe the use of magnetically active beads and magnetic forces to selectively remove non-specifically bound beads (BARC). U.S. Pat. Nos. 6,086,821 and 6,368,553 describe the use of ultrasonic energy to provide a variable force for measuring the binding forces between molecular entities and for sensing the presence of an analyte in a test sample. The above referenced patents are incorporated by reference in their entirety.

In many binding assays it is common practice to use some type of rinsing step for the purpose of reducing the background signal. Common rinsing methods include soaking with our without mechanical agitation and spraying with non-steady flow. Under these poorly controlled conditions smaller particles are removed with greater difficulty because of the no-slip boundary condition at the walls. For sufficiently large fluid boundary dimensions and flow velocities, fluid inertia leads to turbulent flow that can enhance particle removal. At small enough fluid boundary dimensions and velocities, however, the flow is determined by viscosity alone, leading to a steady, laminar flow that does not easily remove particles from surfaces. The two regimes are characterized by the Reynolds number, $R_e = \rho dv/\eta$, where $\rho$ is the fluid density, d is the characteristic dimensions of a channel (volume/surface area), v is the fluid velocity, and $\eta$ is the viscosity. For particles or channels less than 1 mm wide and velocities less than 1 mm/s, $R_e$ is less than 1 and the flow is definitely laminar. The dividing line between laminar and the beginning of turbulent flow is at $R_e \sim 2000$. Laminar flow conditions commonly occur in blood vessels and in the microfluidics systems used in many biosensor systems.

Viscous hydrodynamic forces on particles at a wall have been studied with the goal of understanding cell adhesion. For example, the migration of white blood cells occurs (via molecular control) as a slow sticky-rolling detachment along blood vessel walls. Chang and Hammer, *Langmuir*, 1996, 12, 2271-2282 developed a lever amplification model and simulated forces on molecules binding particles to a wall in fluid flow tangential to the binding surface. Zocchi observed the normal force components on 4.5 μm-diameter particles in a tangential flow (*Biophysical J.* 2001, 81, 2946-2953). He measured a lever amplification of the flow forces and observed the rupture of biotin-streptavidin bonds and applied the results to the interpretation of cell adhesion assays.

SUMMARY OF THE INVENTION

This invention describes a simple, versatile method of controllably removing non-specifically bound micrometer-scale particle labels in a binding assay using fluidic flow drag forces, which we will call fluidic force discrimination (FFD). FFD can only be achieved using specific ranges of label sizes and flow conditions. FFD can be used with a wide variety of label types and associated detection methods, improving the sensitivity and selectivity of a broad range of solid-phase binding assays. FFD could also be potentially used to apply controlled, variable forces to identify or separate different targets based on the force required to rupture bonds between a plurality of particle-labeled targets and the substrate-bound receptors.

FIGURES

FIG. 1. depicts capture molecules specific to different targets separately immobilized on a substrate with built in sensors for the label particles.

Figure 2:
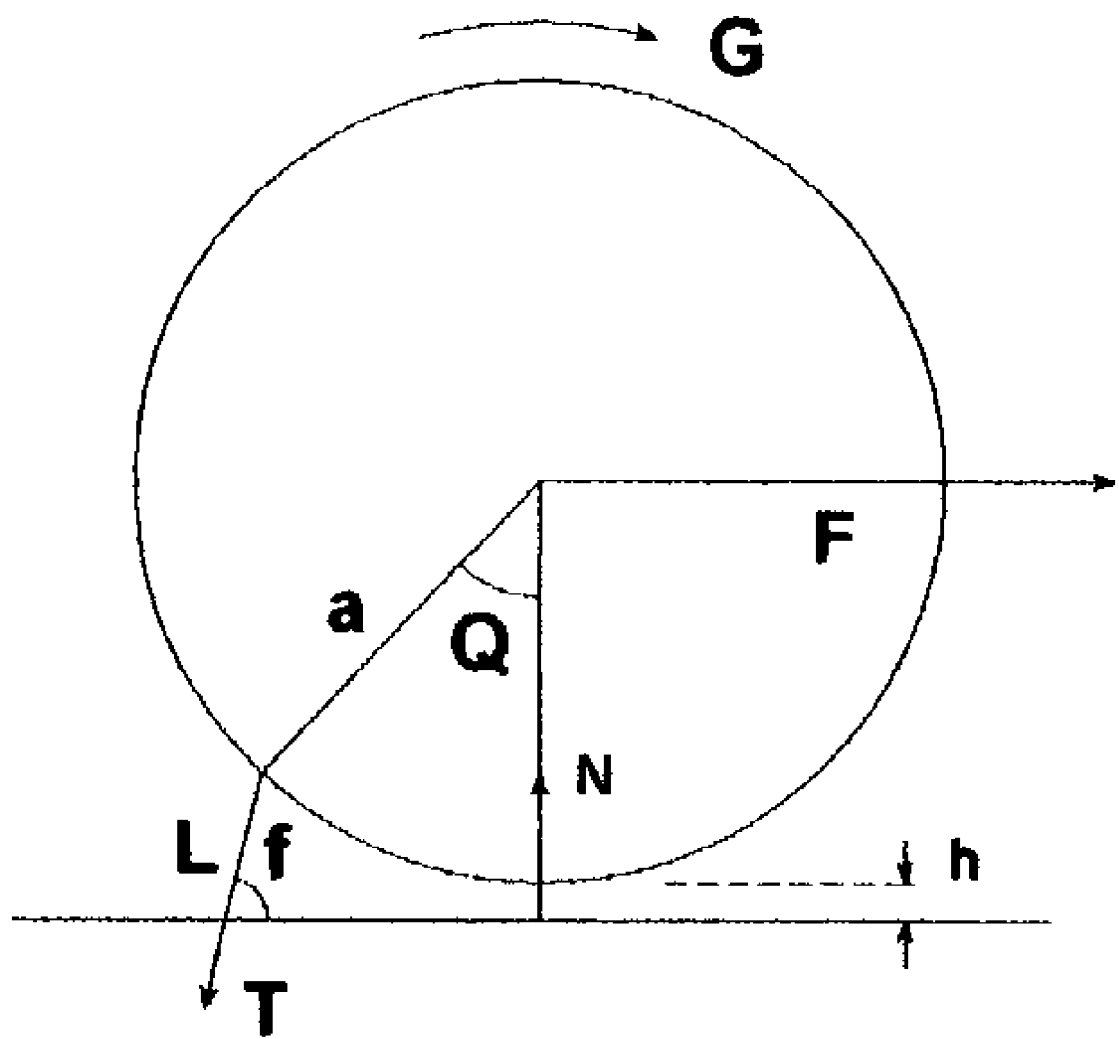

FIG. 2. depicts the lever action and resultant tension, T, in a molecular tether.

Figure 3:
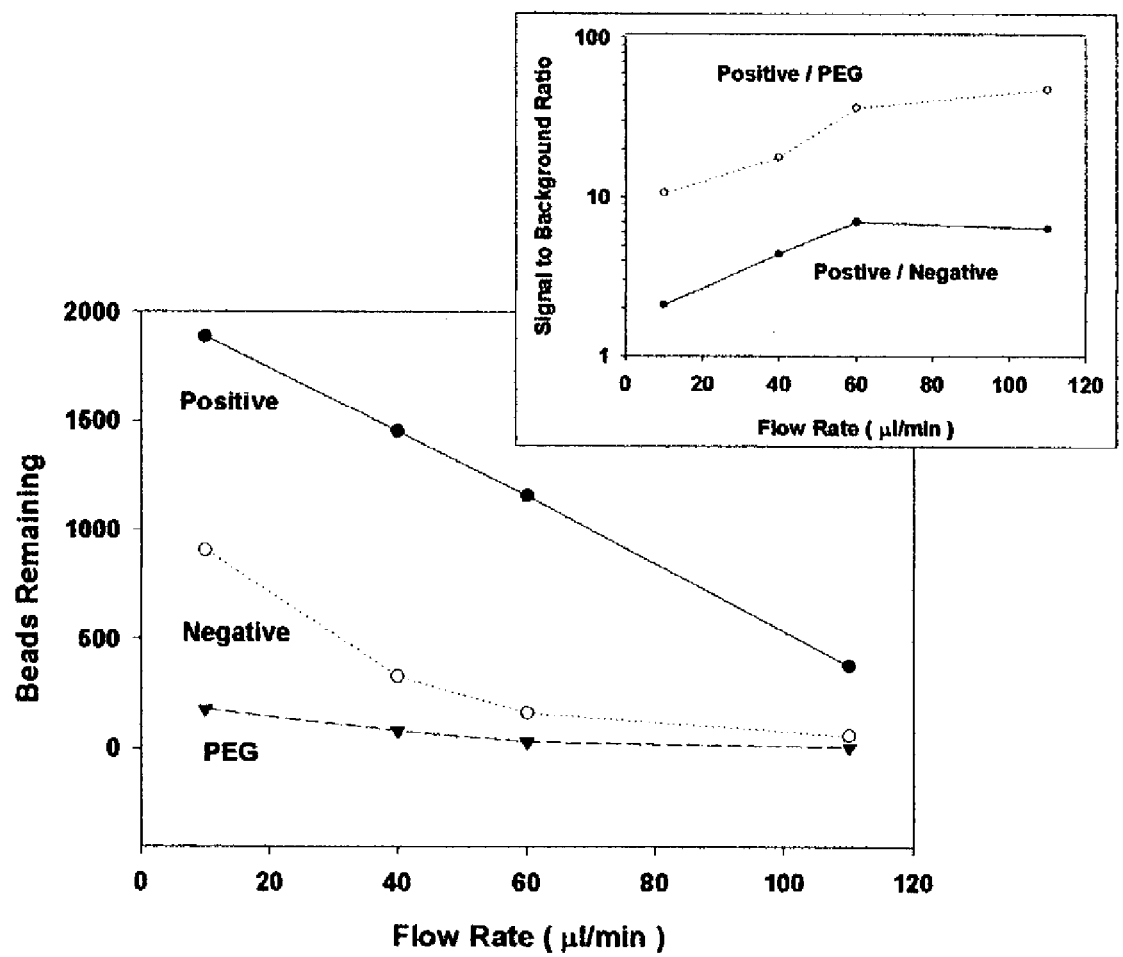

FIG. 3. depicts the action of FFD on non-specifically bound beads which influences remaining beads and signal to background ratios for beads used in the assay of the invention.

Figure 4:
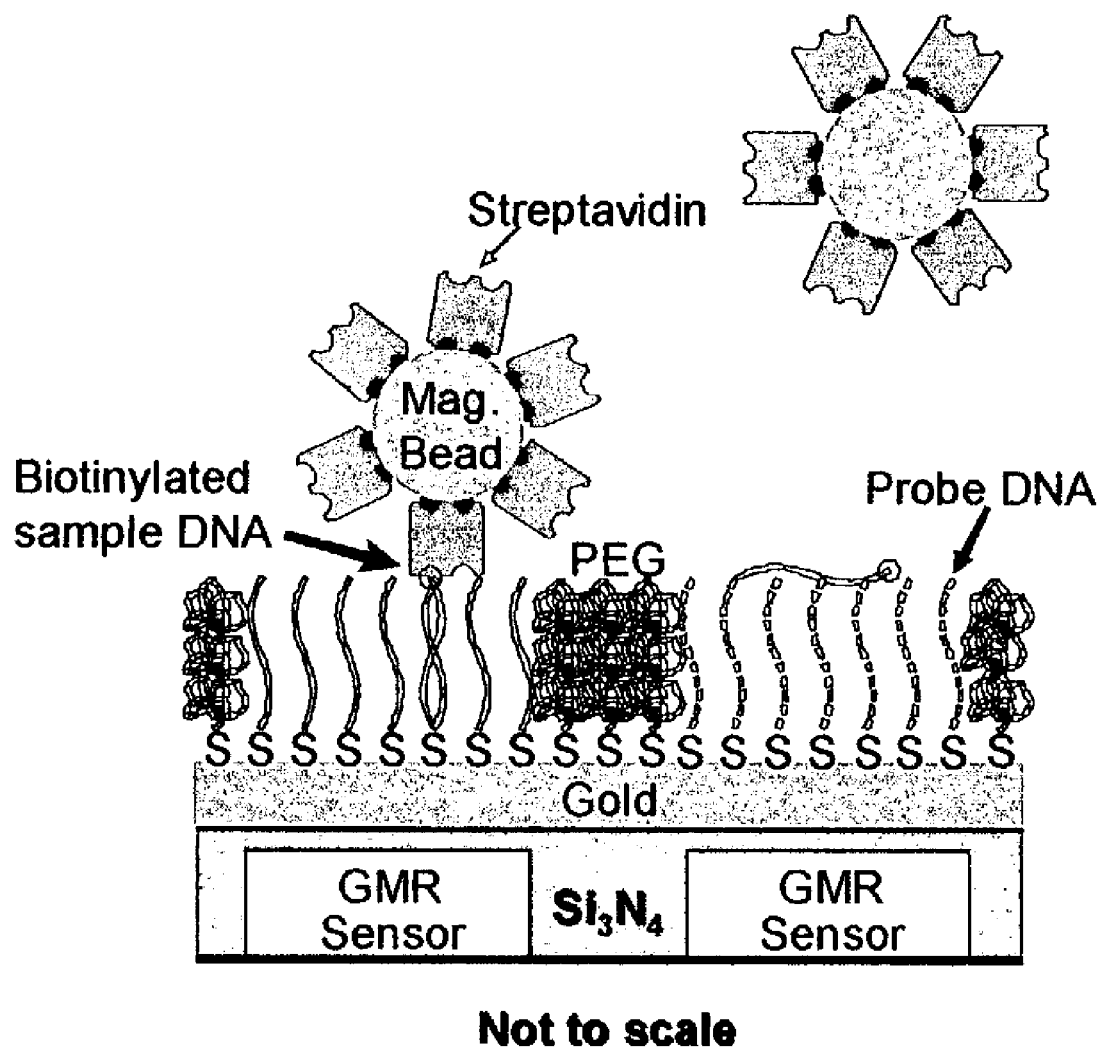

FIG. 4. depicts the assay described in the experimental demonstration of this invention. Note that the figure is not to scale.

DETAILED DESCRIPTION OF THE INVENTION

1. Definitions

Biomolecular recognition has been widely discussed in the scientific literature. The terms ligand and receptor are most often used with protein recognition such as antigen-antibody, but in the invention described herein, we shall take a broader definition that also includes but is not limited to specific molecular recognition of enzymes and substrates, chelators and ions, and complementary strands of polynucleic acids DNA, RNA, and PNA.

2. Theory and Advantages

The present invention uses tangential laminar fluidic forces on particles or beads bound to a surface to selectively break the bonds binding the beads. In particular, FFD can remove a background of more weakly attached, non-specifically bound beads. Under laminar flow, the fluid velocity and associated viscous fluidic force on a particle is greatly reduced at a surface. Solving the Navier-Stokes equation for laminar flow in a tube, for example, leads to parabolic variation of axial fluid velocity across the fluid channel. But near the wall, the velocity increases linearly from zero with distance z away from the wall. Dropping higher order terms, the velocity is given by $v=4uz/R$ for $z \ll R$, where u is the mean velocity in the channel, z is the distance from the wall, and R is the tube radius. The force on a stationary particle in bulk fluid flow is given by the Stokes drag $F_s = 6\pi\eta a v_c$, where a is the particle radius and $v_c$ is the fluid velocity at the particle center. Similarly the torque in bulk fluid with uniform shear is $\Gamma_s = 4\pi\eta a^2 v_c$. Exact laminar solutions for a stationary particle at a wall in a semi-infinite fluid give $F_e = 1.7005 \cdot 6\pi\eta a v_c$ and $\Gamma_e = 0.94399 \cdot 4\pi\eta a^2 v_c$, Goldman et al. *Chem. Engr. Sci.*, 1967, 22 653-660.

For particles bound to a surface by a flexible molecular "tether," there can be a lever amplification of this Stokes force and associated torque acting on the particle. The lever action and resultant tension, T, in the molecular tether is illustrated in FIG. 2. Here the tether bends or pivots and the particle then makes sliding contact downstream at a height difference of h above the tether/wall attachment point. The height h varies with the surface roughness of the wall and bead. For a bead of radius, a, in the micrometer range and a biomolecular tether of much smaller length, L~10 nm, the angle between the tether attachment and bead contact, $\theta$, is small and the angle of the tether, $\phi$, is close to 90 degrees. In this case, the tangential force balance is $F = T \cos \phi$ and the normal force balance is $N = T \sin \phi$, where N is the force the surface exerts on the bead. The torque balance about the particle center yields $\Gamma = -aT \cos(\phi+\theta)$. With the geometrical condition $(L-h)\sin \phi = a\theta^2/2$, small $\theta$, and $\phi$ almost 90 degrees, the tension on the molecular tether is $$T \cong \left(F_e + \frac{\Gamma_e}{a}\right)\sqrt{\frac{a}{2(L-h)}}.$$

For a 1.4 μm-radius bead and a 10 nm tether, the tension creates a lever amplification of the purely tangential fluidic force of about ten times. Overall, given the linear velocity gradient near surfaces, the Stokes linear particle size dependence, and the lever action, the tension is proportional to $a^{2.5}$. For a smooth, 1.4 μm-radius bead at a wall where the velocity at the bead center is 100 μm/s, the exact Stokes force is 4.5 pN and the total amplified tension (including the torque from the 10 nm tether) is 51 pN. This force is over 100 times larger than the normal force ~0.3 pN exerted by a large, high magnetic field NdFeB magnet on a commercial paramagnetic particle of the same size, Edelstein et al., *Biosensors and Bioelectronics*, 2000, 14, 805-813. Note that multiples of the single tether rupture force may be required to remove beads bound with more than one tether, although the density of binding sites on the bead and/or substrate surfaces can be adjusted to greatly reduce the probability of multiple bead-surface bonds.

The application of force to biomolecular bonds, and in general chemical bonds, decreases the energy barrier to dissociation. Therefore, the thermally-activated dissociation rate of chemical bonds exponentially decreases with binding energy but exponentially increases with the application of an external force, as originally discussed by Bell, *Science*, 1978, 200, 618-627. The dissociation rate k is given by $$k = v_0 e^{-\frac{E_b}{kT}} e^{\frac{Fx}{kT}},$$

where $v_0$ is the attempt frequency, $E_b$ is the binding energy, F is the force or tension T on the bond, x is the bond length extension for the transition-state at the top of the dissociation barrier (referred to as the "barrier length" and typically 0.1 to 1.5 nm), and kT is the thermal energy (4.1 pN·nm at 25° C.). Thus, the dissociation rate can be increased ~100 times with the application of a ~100 pN force (assuming x~0.2 nm). Such effects have been observed experimentally using forces applied mechanically with an atomic force microscope, Lee et al., *Langmuir*, 1994, 10, 354-357; Merkel et al., *Nature*, 1999, 397, 50-53; Evans, *Annu. Rev. Biophyis. Biomol. Struct.* 2001, 30, 105-128.

Laminar fluidic force removal of particles enables much more uniform and controlled fluidic forces than conventional rinsing methods. Significantly, the forces can be controlled by choice of specific particle size and flow conditions (flow rate and channel geometry). For particle-labeled binding assays, using FFD to selectively remove non-specifically bound particles and thereby enable a lower number of specifically bound labels to be detected with confidence has many advantages over other discrimination methods. In particular, because many of the most sensitive assay approaches already include a fluidic system, FFD can be easily implemented by proper design of the fluidics, therefore removing the requirement for external rinsing, reducing the assay time and simplifying the assay protocol. A significant advantage of FFD is that it can be used with any type of particle label of appropriate size and functionality, including but not limited to fluorescent, luminescent, light-scattering, magnetic, or radioactive.

Compared to magnetic force discrimination methods, FFD does not require paramagnetic beads or an external magnet field source. In addition, currently available commercial paramagnetic particles can only generate forces in the ~1 pN range, insufficient for force discrimination between specific ligand-receptor bonds. Compared to ultrasonic force discrimination, FFD does not require a separate apparatus for generating ultrasonic energy, and avoids potential problems associated with internal flow cell acoustic reflections causing a variation in the magnitude of local ultrasonic forces as a function of position along a wall.

3. Experimental Demonstration—DNA Hybridization Assay with Microbead Labels

The initial observation of FFD was made using Dynal M280 microbead labels (Dynal, Oslo, Norway). The substrate was a microsensor chip fabricated on a silicon wafer and then covered with a 40 nm-thick gold film. The gold coating was required for covalent attachment of the biomolecules using thiol bonds (S-Au). After coating with gold, the chips were stored in a dry Nitrogen chamber. The chip surfaces were cleaned before use by rinsing with ethanol and distilled water.

Spots of single-stranded DNA (ssDNA) oligonucleotide receptors (10 μM in 400mM potassium phosphate, pH 7.0) 250 μm in diameter were deposited onto the surface using Rapidograph® pen tips, Sheehan et al. *Biosensors and Bioelectronics*, 2003, 18, 000. Two alkanethiol-terminated ssDNA capture receptors were used for the experiment. The positive capture receptor, a 25-base-long ssDNA sequence complementary to the ssDNA target, was terminated on the 3' end with six additional adenine nucleotides and three alkane spacers followed by the thiol. The negative capture receptor was a 24-base-long ssDNA sequence non-complementary to the target with 3 alkane spacers and a thiol on the 3' end. After spotting, the chip was left for eight hours in a humid chamber at 37° C. to allow the ssDNA to immobilize onto the Au surface. (It is unclear whether the length of time in the humid chamber is critical.)

A flow cell made of PDMS (polydimethylsiloxane), a transparent elastomer, was attached to the chip surface with double-sided adhesive tape so that fluid could be flowed through the cell directly in contact with the chip surface. The flow cell had a cross-section of 100 μm high by 2.89 mm wide perpendicular to the flow and a length of 4.4 mm in the direction of the flow. The chip and flow cell were mounted on an upright microscope with sufficient magnification to directly observe the presence and flow of individual beads within the flow cell and on the surface. The microscope was equipped with a video camera connected to a computer for digital image recording. The reagents were pumped through the flow cell at controlled rates with a peristaltic roller pump.

Thiolated PEG (5000 MW polyethylene glycol, Shearwater, Huntsville, Ala.) was introduced over the surface in the flow cell at a concentration of 10 mg per mL deionized (DI) water and let stand for 1 hour. The PEG formed a non-fouling region between the capture receptor spots of DNA. The application of PEG was not necessary for the assay but reduced the non-specific binding of target ssDNA and bead labels outside of the intended capture spots, thereby increasing the number of target ssDNA and beads available to bind within the capture spots.

2×SSC buffer (0.3 M NaCl, 30 mM sodium citrate, pH 7.0) with 0.25% sodium dodecyl sulfate (SDS) was introduced and allowed to stand for 30 minutes. The salt and detergent buffers used here and in subsequent steps enhanced hybridization efficiency and reduced hydrophobic aggregation.

Target ssDNA (100 pM in 2×SSC with 0.25% SDS), complementary to the positive capture receptor ssDNA, was flowed over the surface at a rate of 2 μL/min for 15 minutes to allow for hybridization. The target ssDNA molecules were biotinylated so that they could be directly labeled with streptavidin-coated microbeads (one microbead/DNA) after being captured via hybridization. The ssDNA target was composed of a 25-base-long sequence complementary to the capture receptor terminated on the 3'end by six adenine nucleotides and a biotin molecule. A hybridized target-capture DNA molecule was about 12 nm long from the Au-S bond to the biotin.

Streptavidin coated Dynal M280 microbead labels, 2.8 μm in diameter, were introduced from an aliquot with concentration of greater than or equal to $7 \times 10^6$ beads/cm$^3$ in 1×SSC with 0.125% SDS. Start/stop cycles of 10 seconds of flow at a flow rate of 10 μL/min followed by 50 seconds at zero flow rate to allow the beads to settle deposited approximately 200 beads/200 μm diameter circular spot per cycle. After fifteen 1 min cycles, approximately 2000 beads were within a 200 μm diameter capture spot.

FFD was then used to selectively remove the more weakly attached, non-specifically bound beads as plotted in FIG. 3. 1×SSC buffer with 0.125% SDS was flowed through the cell for 3 min at each of the following flow rates: 10, 40, 60, and 110 μL/min. After each 3 min period the flow was stopped and the number of beads was counted within the 200 μm diameter spots containing the positive and negative capture receptors and within an equivalent area on the PEG coated gold between the capture spots. For the flow cell cross-section used and assuming 10 nm tethers and smooth surfaces, these flow rates generate respective fluid velocities at the center of each microbead of 48, 193, 290, and 532 μm/s; shears of 34, 138, 207, 380 s$^{-1}$; calculated Stokes forces $F_e$ of 2.1, 8.6, 13, and 24 pN; and tether tensions (including torque) of approximately 25, 99, 149, and 273 pN. As shown in FIG. 3, the relative the number of beads specifically bound on a positive capture spot compared to the number bound non-specifically on either a negative spot or on the surrounding PEG-coated surface increases as the flow rate is increased to 60 μl/min. The increase is caused by the relatively greater decrease in the number of beads bound to the negative spot and PEG-coated areas; i.e. those bound by non-specific interactions. The decrease in the number of beads in the positive spot can be attributed to a number of effects. First, there may be some beads non-specifically bound to ssDNA receptors that have not captured target ssDNA (beads whose removal is desirable), which are expected to come off at lower flow rates/ forces. As the flow rate and forces increase, some biotin-streptavidin bonds may also rupture. Under mechanical AFM forces, these bonds rupture at about 200 pN. Note that shear rupture of the much stronger Watson-Crick base-pairing in the DNA is unlikely under these conditions (the corresponding AFM rupture forces are >1 nN).

4. Preferred Embodiments

Given a large enough flow rate or bead diameter, or a short enough molecular tether, FFD in principle can generate enough force to break any chemical bond. In most practical applications, FFD can be used to identify or separate according to the required rupture force populations of molecules bound to a surface by a plurality of different bond strengths as long as the difference in the binding strengths is larger than variations in the force-times-barrier lengths. Force variations would include those caused by roughness or shadowing of flow across one bead by a nearby upstream bead. For molecules with dissociation energetics that include multiple potential energy wells, such as many biological macromolecules, FFD using pulsed flow could potentially remove a relatively greater number of more weakly bound micro-particle labels than strongly bound ones because of the relatively longer times required to cross multiple energy barriers. FFD could also be used as a step in preparing a surface with a specific type or types of molecules from a surface with an initial mixture of a plurality of molecules by selectively attaching microparticle labels to only those types to be removed. After FFD, chemical methods (e.g., a change in pH) could be used to remove the label. Similarly, FFD could be used to adjust the density of molecules on a surface by randomly attaching labels to some fraction, removing them by FFD, and then removing the labels.

The following requirements for FFD focus on its use in biomolecular binding assays, but similar requirements apply to a wider range of potential applications.

FFD can be applied to a wide range of binding assays based on molecular recognition. Primary examples are hybridization of target ssDNA with its complement, as in the experimental demonstration described herein, and antigen-antibody immunological assays. To eliminate the requirement that a target be separately functionalized (e.g., with biotin), binding assays can be performed in a "sandwich" configuration. For example, for a hybridization assay, the capture ssDNA on the surface can be make shorter than the target so that the label can be attached to the free end of the captured target through another ssDNA probe complementary only to that free end. Similarly, in an immunoassay the label can be attached through a second antibody specific to a second, exposed region of the target antigen (a second epitope). A person skilled in the art of binding assays would know that there are a multitude of methods to attach a microparticle label to a target species captured on a surface.

Any surface material can be used in FFD as long as it is suitable for a binding assay. A person skilled in the art of binding assays would know there are a multitude of substrates and corresponding chemical methods to attach useful capture molecules to said substrate surfaces. FFD will be produce the most uniform forces when the substrate surface is flat and smooth, with a height deviation, h, less than the tether length, L, over a spatial distance along the surface approximately equal to the bead radius. The smoothness reduces the variation in tension and removal rates among the particle labels. For example, for 2.8 μm-diameter beads and typical biomolecular tethers of length 10 nm, an h<2 nm over a 1.4 μm area of the surface will assure a <12% variation in tension. Although not a requirement for FFD, this beneficial level of smoothness is not difficult to obtain for a person skilled in the art of substrate preparation.

The requirements for FFD are well matched to the combination of ~1 μm scale beads commonly used (and commercially available) in biomolecular binding assays and separations, and the ~100 μm scale channels typically used in microfluidics systems. The smallest bead size useful for FFD is determined by the maximum flow velocities that are, in turn, constrained by either the maximum pressure tolerable in the microfluidic system or, ultimately, by the maximum Reynolds number of about 2000 for controllable laminar (non-turbulent) flow. The pressure constraint would typically limit the bead size for small height (<130 μm) channels, with the creation of turbulence at high flow rates limiting the bead size for larger channels. To quantify this, the velocity at the height of the bead center, a, through a high-aspect ratio rectangular flow cell like with height s, width w, length, l, and volumetric flow, Q, is given for a<<h and w>>s to a good approximation by $$v_c = 6\frac{Qa}{s^2 w}.$$

For pressure driven flow, Q can be written as $$Q = \frac{s^3 wP}{12\eta l},$$

where P is the pressure differential across the cell length and η, is the viscosity. From the above expressions for tension, the exact Stokes force, and exact torque, the bead radius required to produce a given tension on a tether of length L is given by $$a^{2.5} = \frac{Tl\sqrt{(L-h)}}{15.5\ Ps}.$$

The equation for a tube of radius R with a<<R is the same except R replaces s.

The data in FIG. 3 show that the largest ratio of the positive label binding to the negative label binding occurs in our experiment at a flow rate of 60 μL/min. For the 2.8 μm-diameter beads used, this flow rate translates into a tension force on a 10 nm tether with h=0 of about 150 pN. Smaller beads would require a higher pressure, greater flow cell height, or shorter tether to achieve the same tension force. For example, with our experimental flow-cell (with currently typical microfluidic dimensions), increasing the pressure 5500 times to the practical microfluidics pressure limit of 1 atmosphere would generate similar tension forces on 90 nm-diameter beads. Note, however, that these conditions would require an unpractical flow rate of 330 ml/min.

If higher pressures and flow rates were practical, for small channel heights the particle size limit is given by the requirement for laminar flow, $$a^{2.5} = \frac{Ts^2\sqrt{(L-h)}}{7.45 \times 10^5 \eta^2}.$$

For tension greater than or equal to 150 pN and the flow cell dimensions in the experimental test case, this corresponds to a requirement for beads of diameter >66 nm. Note that nanometer-scale labels are generally more difficult to detect then micrometer-scale labels. Conversely, although beads>10 μm in diameter are generally easier to detect, the reduction in labels/surface area reduces the dynamic range in binding assays. In addition, larger beads require much lower flow rates to achieve force discrimination, greatly increasing the time required to introduce the labels (and the binding assay overall), which is an undesirable effect.

Although the examples presented in detail have used rectangular fluidic channels, this is not a requirement for FFD.

The flow cell can take a variety of enclosed forms, and flow could even be in an open channel. The required fluidic conditions could also be achieved by moving the substrate through a fixed fluid volume. Instead of tangential flow across a substrate surface, FFD could also be achieved with fluid flow through and normal to a porous membrane on which beads were bound to the surface (although there would be no lever amplification of forces on the molecular tethers for this normal force).

The invention claimed is:

1. A method for improving the sensitivity and selectivity of analyte detection in a binding assay labeled with micrometer-scale particles, comprising carrying out a binding assay wherein a capture surface capable of binding by specific molecular recognition an analyte of interest is exposed to a sample to be tested and to a detectable micrometer-scale particle label capable of binding by specific molecular recognition to said analyte or to an intervening receptor that binds specifically to the analyte and to the micrometer-scale particle label, wherein if said sample contains said analyte, said analyte is bound by specific molecular recognition to said capture surface and also bound by specific molecular recognition to at least one said particle label;

applying a controlled and uniform laminar flow at said capture surface, said flow producing a Stokes force on said particle labels of at least 1 pN, wherein said Stokes force preferentially removes said particle labels at said capture surface that are not specifically bound to said analyte specifically bound to said capture surface, wherein said flow operates normally through a porous substrate on the surface of which said particle labels are bound; and detecting said particle labels specifically bound to said analyte specifically bound to said capture surface.

2. A method for improving the sensitivity and selectivity of analyte detection in a binding assay labeled with micrometer-scale particles, comprising carrying out a binding assay wherein a capture surface capable of binding by specific molecular recognition an analyte of interest is exposed to a sample to be tested and to a detectable micrometer-scale particle label capable of binding by specific molecular recognition to said analyte or to an intervening receptor that binds specifically to the analyte and to the micrometer-scale particle label, wherein if said sample contains said analyte, said analyte is bound by specific molecular recognition to said capture surface and also bound by specific molecular recognition to at least one said particle label;

applying a controlled and uniform laminar flow at said capture surface, said flow producing a Stokes force on said particle labels of at least 1 pN, wherein said Stokes force preferentially removes said particle labels at said capture surface that are not specifically bound to said analyte specifically bound to said capture surface, wherein the flow is pulsed from a flow rate that applies a lower Stoke force to said particle label to a higher flow rate that applies a higher Stokes force to said particle label for at least one period of time to effect greater removal of said non-specifically bound particles; and detecting said particle labels specifically bound to said analyte specifically bound to said capture surface.

* * * * *